United States Patent [19]

Baasner et al.

[11] Patent Number: 5,093,532

[45] Date of Patent: Mar. 3, 1992

[54] PROCESS FOR THE PREPARATION OF HALOGENOMETHYLKETONES, IN PARTICULAR OF 1,1,1-TRIFLUOROACETONE

[75] Inventors: Bernd Baasner, Bergisch Gladbach; Jens Lorentzen, Cologne, both of Fed. Rep. of Germany

[73] Assignee: Bayer Aktiengesellschaft, Leverkusen, Fed. Rep. of Germany

[21] Appl. No.: 739,112

[22] Filed: Jul. 31, 1991

[30] Foreign Application Priority Data

Aug. 9, 1990 [DE] Fed. Rep. of Germany ....... 4025188

[51] Int. Cl.$^5$ .............................................. C07C 45/50
[52] U.S. Cl. .................................. 568/407; 568/323; 560/174
[58] Field of Search ................. 568/407, 323; 560/174

[56] References Cited

PUBLICATIONS

J. Chem. Soc., p. 835, (1950).
J. Chem. Soc., p. 1273 (1954).

*Primary Examiner*—James H. Reamer
*Attorney, Agent, or Firm*—Sprung Horn Kramer & Woods

[57] ABSTRACT

Halogenomethylketones are prepared from nitro compounds by treating the latter in alcoholic solution with sodium alkoxide or potassium alkoxide, cooling to a temperature in the range $-10°$ to $-100°$ C. and then allowing the mixture to react with ozone at $-10°$ to $-100°$ C. The process is particularly suitable for the preparation of 1,1,1-trifluoroacetone from 1,1,1-trifluoro-2-nitropropane.

9 Claims, No Drawings

PROCESS FOR THE PREPARATION OF HALOGENOMETHYLKETONES, IN PARTICULAR OF 1,1,1-TRIFLUOROACETONE

The present invention relates to a particularly advantageous process for the preparation of halogenomethylketones. Halogenomethylketones, in particular 1,1,1-trifluoroacetone, are important intermediates for the preparation of biologically active compounds (see, for example, J. Med. Chem. 1975 (18), 895, J. Med. Chem. 1983 (26), 950 and Bull. Soc. Chim. France 1986, 933).

Processes for the preparation of halogenomethylketones, in particular of 1,1,1-trifluoroacetone, have already been disclosed. Thus, starting from methyl trifluoroacetate, trifluoroacetone can be prepared by condensation with ethyl acetate and subsequent acid-catalysed cleavage of the ethyl trifluoroacetoacetate formed as an intermediate. Owing to self-condensation of the ethyl acetate, high proportions of by-products are formed (yield of desired product only 54%) and long reaction times are moreover required (See Bull. class. Sci. Acad. roy. Belg. [5]12, 692 (1926); Bull. Acad. Belg. [5]13, 175; J. Am. Chem. Soc. 69, 1819 (1947); J. Am. Chem. Soc. 74, 1426 (1952)).

In the treatment of trihalogenoacetic acids with alkylmagnesium bromides in dibutyl ether, trihalogenomethyl alkyl ketones are obtained (see J. Chem. Soc. 1956, 835). Similarly, in the treatment of trifluoromethylmagnesium iodide with acetyl chloride or acetonitrile in dibutyl ether, 1,1,1-trifluoroacetone is obtained (see J. Chem. Soc. 1954, 1273).

Other known processes for the preparation of 1,1,1-trifluoroacetone are the mercury(II) salts-catalysed reaction of 3,3,3-trifluoropropine with aqueous methanol (see J. Am. Chem. Soc. 74, 650 (1952)) or aqueous sulphuric acid (see J. Chem. Soc. 1952, 3483) and the oxidation of 1,1,3,3,3-pentafluoro-2-methyl-propene with potassium permanganate in acidic aqueous solution (see J. Chem. Soc. 1953, 3565).

The disadvantage of these processes is that the required starting materials are only accessible by complicated syntheses and are therefore very expensive (for example 3,3,3-trifluoropropine), reactions which are difficult to handle industrially have to be carried out (for example Grignard reactions), auxiliaries necessitating particular outlay ecologically are required (for example mercury salts) and/or low yields result.

A process has now been found for the preparation of halogenomethylketones of the formula (I)

in which
X represents halogen,
n represents 1, 2 or 3 and
R represents optionally substituted $C_1$–$C_{20}$-alkyl,
which is characterised in that a nitro compound of the formula (II)

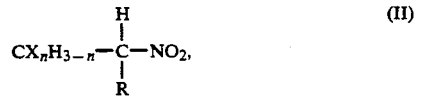

in which
X, n and R have the meaning indicated in formula (I),
is treated with sodium alkoxide or potassium alkoxide solution in alcohol, cooled to a temperature in the range $-10°$ to $-100°$ C. and the mixture is then allowed to react with ozone at $-10°$ to $-100°$ C.

Suitable alcohols are, for example, methanol, ethanol, isopropanol, propanol, n-butanol, t-butanol, sec.-butanol, pentanol and/or iso-amyl alcohol.

Suitable alkoxide solutions are solutions of sodium alkoxides or potassium alkoxides in any desired alcohols. Sodium alkoxides or potassium alkoxides having 1 to 4 C atoms in combination with one of the abovementioned alcohols as solvents are preferred. Solutions containing sodium methoxide or potassium methoxide in methanol are particularly preferred.

In the formulae (I) and (II), X, for example, can represent fluorine, chlorine and/or bromine It preferably represents fluorine. n preferably represents 2 or 3, particularly preferably 3.

If R denotes a substituted alkyl radical, suitable substituents are, for example: halogen atoms, aryl groups having 6 to 10 C atoms, C=O groups, COOR' groups where R'=$C_1$–$C_6$-alkyl and acetal groups of the formula (III)

R preferably represents $C_1$–$C_6$-alkyl which is optionally substituted by fluorine, chlorine, bromine, phenyl, substituted phenyl, naphthyl and/or substituted naphthyl. R particularly preferably represents methyl, ethyl, propyl, butyl or pentyl, very particularly preferably methyl. That is to say, 1,1,1-trifluoroacetone is very particularly preferably prepared according to the invention from 1,1,1-trifluoro-2-nitro-propane.

The compounds of the formula (II) required as starting materials are obtainable, for example, according to EP-A 116,885 and according to EP-A 116,886 or in an analogous manner thereto.

The process according to the invention can be carried out by first dissolving the compound of the formula (II) in alcohol which is as anhydrous as possible and then adding sodium alkoxide or potassium alkoxide in solid form or dissolved in an alcohol. Sodium alkoxide or potassium alkoxide can be employed, for example, in amounts of 0.8 to 1.2 mol per mol of compound of the formula (II). 0.9 to 1.1 mol of sodium alkoxide or potassium alkoxide are preferred, in particular 1 mol of sodium methoxide, in each case relative to 1 mol of the compound of the formula (II).

The addition of the alkoxide can be carried out, for example, at temperatures in the range $-80°$ to $+60°$ C., preferably at $-20°$ to $+40°$ C.

Before the addition of the ozone, the reaction mixture is cooled to $-10°$ to $-100°$ C., preferably $-50°$ to $-78°$ C., and then reacted with ozone at a temperature in these ranges.

Ozone can be added, for example, as a gas, for example introduced into the reaction mixture in a mixture with oxygen, or in dissolved form, for example dissolved in one of the abovementioned alcohols. In order to ensure a complete conversion, it is advantageous to employ ozone in at least equimolar amounts, relative to the compound of the formula (II). For example, 1 to 1.2 mol of ozone can be employed relative to the compound of the formula (II), it being possible to detect a slight excess of ozone from a persisting blue coloration of the reaction mixture.

The reaction mixture can then be worked up by allowing it to warm to room temperature and blowing out excess ozone which may still be present before, during and/or after warming to room temperature, for example with nitrogen or another inert gas. The halogenomethylketone of the formula (I) formed is in general present as a hydrate, acetal and/or hemiacetal in the mixture then remaining. For many other reactions, the halogenomethylketone of the formula (I) thus prepared can be employed in the form of the mixture remaining after warming to room temperature and if desired blowing out excess ozone.

Such mixtures can also be worked up to isolate the halogenomethylketone of the formula (I) formed. In this case, for example, if desired after addition of dimethyl sulphide, easily volatile constituents, in particular methanol, can be evaporated, the residue taken up with ether, the ethereal solution washed with water and/or sodium chloride solution, then dried, for example with sodium sulphate, then concentrated and the halogenomethylketone of the formula (I) prepared isolated by distillation and/or crystallisation.

In the case of the preparation according to the invention of low-boiling, easily volatile halogenomethylketones, for example of 1,1,1-trifluoroacetone having a boiling point of 20° to 22° C., which moreover under the reaction conditions still easily forms the hydrate or the hemiacetal with the respective alcohol, these can be isolated, after the reaction and removal of ozone which may still be present, in pure form by addition of phosphorus pentoxide and subsequent distillation or as an alcoholic solution which as a rule can be employed for subsequent reactions. For some subsequent reactions it is most expedient directly to employ the ozone-free crude solution after a determination of the content of halogenomethylketone. The yields of halogenomethylketones in the preparation according to the invention are in general between 70 and 95%, relative to the nitro compound of the formula (II) employed. The purities of the halogenomethylketones isolated are in this case in general between 82 and 98% (determined by gas chromatography).

It is decidedly surprising that halogenomethylketones of the formula (I) can be prepared so easily in the manner according to the invention as it is known that, for example, an elimination of fluoride takes place from 1,1,1-trifluoro-2-nitro-propane in a basic medium (see U.S. Pat. No. 4,840,969).

EXAMPLES

Example 1

A solution of 10.1 g (70 mmol) of 1,1,1-trifluoro-2-nitro-propane in 100 ml of absolute methanol was treated with 3.87 g (7.2 mol) of solid sodium methoxide and cooled to −78° C. 900 ml of a saturated methanolic ozone solution were then added at the same temperature and the mixture was left at −78° C. for 1.5 hours. Excess ozone was then blown out at −78° C. by means of a stream of nitrogen. 1,1,1-Trifluoroacetone, its hydrate and the hemiacetal with methanol were present in this crude solution according to spectroscopic investigation (IR, Raman, $^1$H-NMR and $^{19}$F-NMR spectroscopy).

After addition of phosphorus pentoxide, the product was then distilled off in methanol at normal pressure at a temperature up to 66° C. The mixture thus obtained can be employed for further reactions without further isolation of the trifluoroacetone.

For further identification to determine the yield, the batch described above was repeated and the solution obtained after the distillation was added dropwise with stirring at 20° C. to a solution of 29.7 g (150 mmol) of 2,4-dinitrophenylhydrazine in 400 ml of 20% strength by weight aqueous sulphuric acid (analogously to J. Am. Chem. Soc. 69, 1819 (1947)). The precipitated 2,4-dinitrophenylhydrazone of 1,1,1-trifluoroacetone was filtered off with suction, washed with water and dried. 17.1 g of the hydrazone having a melting point of 137°–138° C. were obtained. This corresponds to a yield of 83%, relative to 1,1,1-trifluoro-2-nitropropane employed.

Example 2

A solution of 12.3 g (70 mmol) of 1,1-dichloro-1-fluoro-2-nitropropane in 100 ml of absolute methanol was treated with 3.87 g (7.2 mol) of solid sodium methoxide and cooled to −78° C. 900 ml of a saturated methanolic ozone solution were then added at the same temperature and the mixture was left at −78° C. for 1.5 hours. Excess ozone was then blown out at −78° C. by means of a stream of nitrogen. 1,1-Dichloro-1-fluoroacetone, its hydrate and the hemiacetal with methanol were present in this crude solution according to spectroscopic investigation (IR, Raman, $^1$H-NMR and $^{19}$F-NMR spectroscopy).

For further identification and to determine the yield, the batch described above was repeated and the crude solution was added dropwise with stirring at 20° C. to a solution of 29.7 g (150 mmol) of 2,4-dinitrophenylhydrazine in 400 ml of 20% strength by weight aqueous sulphuric acid. The precipitated 2,4-dinitrophenylhydrazone of 1,1-dichloro-1-fluoroacetone was filtered off with suction, washed with water and dried. 10.7 g of the hydrazone having a melting point of 145°–146° C. were obtained. This corresponds to a yield of 83%, relative to 1,1-dichloro-1-fluoro-2-nitropropane employed.

What is claimes is:

1. Process for the preparation of halogenomethylketones of the formula (I)

in which
X represents halogen,
n represents 1, 2 or 3 and
R represents optionally substituted $C_1$–$C_{20}$-alkyl,
in which a nitro compound of the formula (II)

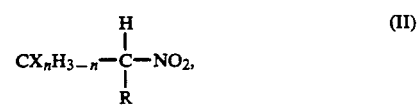

in which
X, n and R have the meaning indicated in formula (I), is treated with sodium alkoxide or potassium alkoxide in an alcohol, cooled to a temperature in the range −10° to −100° C. and the mixture is then allowed to react with ozone at −10° to −100° C.

2. The process of claim 1, in which in the formulae (I) and (II)

X represents fluorine, chlorine and/or bromine, n represents 2 or 3, and

R represents a $C_1$–$C_{20}$-alkyl radical which is optionally substituted by halogen atoms, aryl groups having 6 to 10 C atoms, C=O groups, COOR' groups where R'=$C_1$–$C_6$-alkyl and/or acetal groups of the formula (III)

3. The process of claim 1, in which 1,1,1-trifluoro-2-nitropropane is employed as the compound of the formula (II) and 1,1,1-trifluoroacetone is obtained as the halogenomethylketone of the formula (I).

4. The process of claim 1, in which 0.8 to 1.2 mols of sodium alkoxide or potassium alkoxide are employed per mol of nitro compound of the formula (II) and the alkoxide is added at temperatures in the range −80° to +60° C.

5. The process of claim 1, in which the reaction with ozone is carried out at temperatures in the range −50° to −78° C.

6. The process of claim 1, in which ozone is added as a gas in a mixture with oxygen or dissolved in alcohol.

7. The process of claim 1, in which 1 to 1.2 mols of ozone per mol of the nitro compound of the formula (II) are employed.

8. The process of claim 1, in which excess ozone is blown out after completion of the reaction.

9. The process of claim 1, in which excess ozone is blown out after the reaction, then, if desired after addition of dimethyl sulphide, easily volatile constituents are evaporated, the residue is taken up with ether, the ethereal solution is washed with water and/or sodium chloride solution, then dried and concentrated, and the halogenomethylketone of the formula (I) prepared is isolated by distillation and/or crystallisation.

* * * * *